US011623917B2

(12) United States Patent
Horn

(10) Patent No.: US 11,623,917 B2
(45) Date of Patent: Apr. 11, 2023

(54) MULTI-TYROSINE KINASE INHIBITORS DERIVATIVES AND METHODS OF USE

(71) Applicant: Ontogenesis, LLC, Deerfield, IL (US)

(72) Inventor: Gerald Horn, Deerfield, IL (US)

(73) Assignee: Ontogenesis, LLC, Deerfield, IL (US)

( * ) Notice: Subject to any disclaimer, the term of this patent is extended or adjusted under 35 U.S.C. 154(b) by 307 days.

(21) Appl. No.: 17/118,807

(22) Filed: Dec. 11, 2020

(65) Prior Publication Data

US 2021/0114986 A1 Apr. 22, 2021

Related U.S. Application Data

(63) Continuation of application No. 16/517,879, filed on Jul. 22, 2019, now Pat. No. 10,899,712, which is a continuation-in-part of application No. 15/812,399, filed on Nov. 14, 2017, now Pat. No. 10,464,902, which is a continuation-in-part of application No. 15/711,208, filed on Sep. 21, 2017, now abandoned, which is a continuation-in-part of application No. 15/676,060, filed on Aug. 14, 2017, now abandoned, which is a continuation-in-part of application No. 15/403,139, filed on Jan. 10, 2017, now abandoned, which is a continuation-in-part of application No. 15/402,214, filed on Jan. 9, 2017, now abandoned, which is a continuation-in-part of application No. 15/288,820, filed on Oct. 7, 2016, now abandoned, which is a continuation-in-part of application No. 15/194,813, filed on Jun. 28, 2016, now abandoned.

(60) Provisional application No. 62/185,785, filed on Jun. 29, 2015.

(51) Int. Cl.
*C07D 215/22* (2006.01)
*C07C 233/57* (2006.01)

(52) U.S. Cl.
CPC .......... *C07D 215/22* (2013.01); *C07C 233/57* (2013.01)

(58) Field of Classification Search
CPC ............................ C07D 215/22; C07C 233/57
See application file for complete search history.

(56) References Cited

U.S. PATENT DOCUMENTS

2015/0079089 A1* 3/2015 Wadehra .................. A61P 5/14
424/139.1

* cited by examiner

*Primary Examiner* — Erich A Leeser
(74) *Attorney, Agent, or Firm* — Wood, Phillipe Katz, Clark & Mortimer

(57) ABSTRACT

The present invention is directed to multi-tyrosine kinase inhibitor compounds. The present invention is further directed to compositions comprising those compounds. Finally, the present invention is directed to methods of treating eye conditions including, but not limited to, diabetic background retinopathy, diabetic macular edema, diabetic proliferative retinopathy, diabetic macular edema with proliferative retinopathy, proliferative fibrovascular disease, diabetic macular edema with proliferative fibrovascular disease, retinopathy of prematurity, dry macular degeneration, dry macular degeneration with drusen and wet macular degeneration, using compounds and compositions of the invention.

10 Claims, No Drawings

MULTI-TYROSINE KINASE INHIBITORS DERIVATIVES AND METHODS OF USE

BACKGROUND OF THE INVENTION

Many intraocular diseases, such as proliferative retinopathies, occur due to neovascularization and/or leakage, which are caused in part by elevated vascular endothelial growth factor ("VEGF") levels. These diseases include, but are not limited to, diabetic macular edema, diabetic proliferative retinopathy, retinopathy of prematurity, diabetic vitreal traction, wet macular degeneration and attendant neovascularization through Bruch's membrane between the choroid and retina, branch vein occlusion, complete retinal vein occlusion, maculopathies such as Best's disease, ischemic intraocular insult resulting in neovascular rubeotic (iris, anterior chamber angle neovascularization) glaucoma, and on or within the cornea coinciding with herpes simplex keratitis or a graft rejection.

Diabetic macular edema is the most common cause of vision loss among diabetics. Due to the increase in diabetes (both type I and type II) in developed countries such as the United States, diabetic macular edema is also the most common cause of vision loss among working-aged adults. Diabetic macular edema results when insulin resistance causes the vascular lining of blood vessels to thicken, resulting in capillary drop out, microaneurysms, ischemia, and leakage in the retina. The resulting hypoxia triggers an increase in the production of VEGFs, which in turn is a potent inducer of vascular permeability (leakage) and eventually results in the production of new blood vessels. These leaking blood vessels leak fluid into the macula causing the macula to swell resulting in vision loss, as well as eventually causing new blood vessel growth along the retina and into the vitreous causing proliferative retinopathy with high morbidity from bleeding and retinal detachment from resulting vitreous traction and scarring.

Macular degeneration is a disease of the eye that results in minor to severe impairment of the subject's sharp central vision, which is necessary for activities such as reading and driving. Age-related macular degeneration ("AMD") afflicts an estimated 30 to 50 million people worldwide and is the leading cause of severe vision loss in Western societies. AMD disrupts the photoreceptors of the macula in one of two ways: (1) deposits of extracellular debris between Bruch's membrane and the retinal pigment epithelium known as "dry" macular degeneration and (2) breaks in Bruch's membrane that allow angiogenic blood vessels from the choroid to penetrate the retinal pigment epithelium known as "wet" macular degeneration. Dry AMD progresses slowly and is responsible for about 90% of AMD worldwide. Wet AMD can be sudden, severe and irreversible due to bleeding and scarring of the macular region including the fovea. Although wet AMD accounts for only 10% of AMD worldwide it is responsible for 90% of AMD-associated blindness.

VEGFR pathways are the main pharmaceutical targets of angiogenic suppression. Anti-angiogenesis drugs that target VEGFR pathways and are used in the eye include bevacizumab (Avastin®; Avastin is a registered trademark of Genentech, Inc.), ranibizumab (Lucentis®; Lucentis is a registered trademark of Genentech, Inc.) and recombinant fusion proteins such as aflibercept (Eylea®; Eylea is a registered trademark of Regeneron Pharmaceuticals, Inc.). These anti-VEGF protein drugs, which are too large to formulate for topical applications, require an injection monthly or several times per year to limit further vision loss. Currently, the morbidity, inconvenience, and expense of these injectables limit treatment to only severe pathologic states, because they are too invasive for routine prophylaxis prior to onset of significant pathology. For example, prophylactic administration would benefit wet macular degeneration such as in the presence of confluent or otherwise near confluent macular drusen of dry macular degeneration (a known predisposing risk factor for retinal pigment epithelium layer cracks and choroidal neovascularization). In another example, prophylactic administration would benefit the presence in diabetics of background diabetic retinopathy at various points of disease progression prior to the development of diabetic macular edema (e.g., macular or paramacular exudate, high density of dot blot hemorrhages) and most particularly prior to the development of proliferative retinopathy with or without macular edema such as in the presence of severe capillary drop out, and still more particularly in the presence of proliferative retinopathy prior to the development of fibrovascular retinopathy and attendant retinal traction and epiretinal formation. The inability to use these drugs as a prophylactic treatment modality limits their effectiveness in preventing early vision loss, but rather restricts them largely to treating only existing visual loss that can be extensive even at initial diagnosis.

Once in the vitreous humor these anti-VEGF proteins have a half-life of about 9 days, a high IC50 VEGFR inhibition value, fast release rate due to their hydrophilic nature and immediate dispersion within the vitreous towards tissue receptors, and interact with only one angiogenic receptor, VEGF. All of these qualities result in the need for a variety of formulation techniques required to attempt to enhance the residence time of the drug within the vitreous humor to achieve the more prolonged effect that would add safety and efficacy from a single injection. These formulation techniques include attempts at high concentrations, high volumes of bolus injection, emulsions, encapsulation techniques, and other sustained-release compositions; though their highly hydrophilic nature, relatively high concentrations required for efficacy (IC50 about 19 nM for Lucentis®), and limitations imposed on protein stability within solution restrict their potential for additional sustained duration via direct injection. As a result, although these drugs reduce disease morbidity they still add serious injection related morbidity exacerbated by the high frequency of injections required per year, where such injection induced morbidity includes but is not limited to endophthalmitis (intraocular severe infection often with complete vision loss), cataract, glaucoma, and vitreous traction that for many patients can be devastating.

To achieve 30-day duration of effect requires the maximum injectable volume tolerable by the human eye, about 50 uL, at about 0.50%. Such high bolus volumes frequently result in high intraocular pressure up to 49 mm Hg. Additionally, attempts to overcome these formulation and administration challenges can be problematic limited by properties intrinsic to these protein anti-VEGF molecules. For example, the pathology of the disease to be treated exposes these active agents to a variety of noxious stimuli including a more ischemic and acidic environment, which can cause these proteins to denature and degrade more rapidly and therefore compromise their potency when delivered via a sustained-release device. Particularly, the least invasive class of injectable sustained release implants, such as biodegradeable implants such as Ozurdex®/Pozurdex® (Ozurdex is a registered trademark of Allergan, Inc.) releases glycolic and lactic acid that limit the usefulness of proteins for such devices due to rapid low pH denaturation. Finally, the efficacy of this class of drugs is limited by substantial tachyphylaxis and resistance that develops over time due to their inhibition of only VEGF's and not additional angiogenic receptors.

Additional tyrosine kinase receptors ("ancillary receptors") involved in angiogenesis in addition to VEGFR have also been discovered and found to confer additional antiangiogenic benefit above that of VEGFR only inhibition as seen with protein anti-VEGF drugs such as Lucentis®, Avastin®, and Eylea®. The suppression of these ancillary receptors is known to enhance the anti-angiogenic effect of VEGFR pathway suppression. These ancillary receptors include platelet-derived growth factor receptors ("PDGFR") α and β, fibroblast-derived growth factor receptors ("FDGFR") 1-4, c-KIT, and TIE 1-3, and particularly c-MET. Upregulation of c-MET is known to occur following anti-VEGF treatment and result in tachyphylaxis/resistance to such drugs with expression of angiogenic behavior resulting. Suppression of one or more of these ancillary receptors in conjunction with suppression of a VEGFR, including but not limited to c-MET, is common in the art and is known as multi-receptor tyrosine kinase inhibition. Multi-receptor tyrosine kinase inhibition for treatment of angiogenesis is known to decrease the incidence and severity of tachyphylaxis or resistance in response to suppression of a VEGFR alone. One such multi-tyrosine kinase inhibitor ("MTKI") is cabozantinib (Cometriq®; Cometriq is a registered trademark of Exelixis, Inc.). Cabozantinib inhibits VEGFR2 at nearly ⅟₅₀₀th (0.214%) of Avastin® (bevacizumab, Genentech®/Roche®), with an IC50 of about 35 picomolar ("pM") vs 1400 pM respectively in in vitro angiogenic assays for inhibition of human umbilical vascular endothelial cells ("HUVEC"). Cabozantinib also inhibits to various degrees other angiogenic receptors including PDGFR, FLT, TIE-2, and c-MET and was approved by the U.S. FDA for the treatment of medullary thyroid cancer.

Pharmaceutical use of tyrosine kinase inhibitors ("TKIs") and more specifically MTKI's for intraocular use is complicated by their high permeability through cell membranes, their impermeability in solution and their high degrees of lipophilicity. These complications limit MTKI's ability to be formulated beyond their most common use for oral cancer treatment. Further, MTKI's such as cabozantinib when administered orally may lead to perforation of the colon. Intravenous administration is also problematic due to the short half-life of MTKI's such as cabozantinib.

Intravitreal injection is complicated by the sensitivity of the intraocular structures, particularly the optic nerve and nerve fiber layer of the retina to even low concentrations of solvents that solubilize or help stabilize other formulations such as emulsions. Though the moderate to high lipophilicity typical of this class may confer some resistance to vitreous degradation and prolong duration once injected the small molecular weight of on average about 500 daltons vs. for example Lucentis® at 40,000 daltons is inversely proportional to drug retention and hence duration. All of the molecules used in VEGF inhibition, including multi-receptor tyrosine kinase inhibition have chemotherapeutic application and have a risk of severe systemic side effects with high systemic absorption. This risk remains for intravitreal injection due to the high cell permeability of this class of drugs. Pazopantinib has undergone up to 10 Phase II efficacy trials between 2008 and 2014 for topical ant-VEGF treatment. However, none of the efficacy trials for Pazopantinib are for invitreal administration. The lack of intravitreal administration efficacy trials for pazopantinib is most likely due to its rapid intravitreal clearance estimated to be within hours for its molecular weight.

Thus, while there is a need in the art for a long-lasting effective inhibitor of angiogenesis and vascular leakage within the eye, particularly a safe and prolonged intravitreal, TKI's or MTKI's that have sufficient duration of activity and a reduced incidence of systemic side effects have to date not been discovered. Those MTKI's that have been tested have not met these ideals and have not been successful for this purpose.

SUMMARY OF THE INVENTION

The present invention is directed to a compound comprising:

a multi-tyrosine kinase inhibitor (MTKI), preferably the MTKI has an IC50 of 10 nanomolar ("nM") or less for one or more proteins selected from the group consisting of VEGFR2, c-MET PDGF, FGF, FLT, c-KIT, RON and TIE, more preferably 5 nM or less for VEGFR2, even more preferably 0.5 nM or less and most preferably 0.05 nM or less, yet more preferably the MTKI also has an IC50 for c-Met of 10 nM or less, more preferably 5 nM or less, most preferably 3 nM or less and yet even more preferably the MTKI is selected from the group consisting of cabozantinib, axitinib, cediranib, ponatinib, foretinib, MGCD-265, motesanib, regorafenib, tivozanib and sunitinib, most preferably cabozantinib or foretinib; and a moiety comprising an optionally substituted C2 to C25 alkyl group optionally bound to a peptide or a protein, wherein the moiety modifies the MTKI at one or more nitrogens and or the moiety replaces one or more carbonyl or methoxy groups of the MTKI and wherein if the MTKI has n carbonyl and methoxy groups and n is greater than 1, then n−1 of the carbonyl or methoxy groups are each individually and optionally absent or optionally replaced by hydrogen, oxygen, carbon, potassium, sulfur, phosphorus, nitrogen, a carbonyl, a sulfhydryl, a phosphatyl, an amide, an amine, a quaternary amine, a phosphate, a phosphonate, a sulfate, a sulfonate, a carboxylate and a urethane.

In a preferred embodiment, the peptide is 10 amino acids or less.

In another preferred embodiment, the moiety comprises albumin.

The C2 to C25 alkyl group may be acyclic or heterocyclic and may be substituted at one or more hydrogens and or one or more carbons with polar groups selected from the group consisting of a carbonyl, a sulfhydryl, a phosphate, a phosphatyl, a phosphonate, an amide, an amine, a quaternary amine, sulfate, a sulfonate and a carboxylate. Alkyls may be individually substituted at any carbon in the chain by nitrogen or oxygen.

In another preferred embodiment, the moiety provides binding to vitreous proteins or plasma proteins, preferably albumin.

In another preferred embodiment, the moiety renders the compound amphiphilic.

In another preferred embodiment the carbonyl, the sulfhydryl, the phosphate, the phosphatyl, the phosphonate, the amide, the amine, the quaternary amine, the sulfate, the sulfonate or the carboxylate are individually substituted with a fatty acid or a second alkyl, preferably palmitate.

In another embodiment, the moiety is attached to the MTKI via a linker selected from the group consisting of a bond, an optionally substituted alkyl, an optionally substituted alkyl-O—, a urethane, and esters thereof.

In another preferred embodiment, the polar moiety provides binding to vitreous proteins or plasma proteins, preferably albumin.

In a preferred embodiment, the present invention is directed to a compound of formula (I)

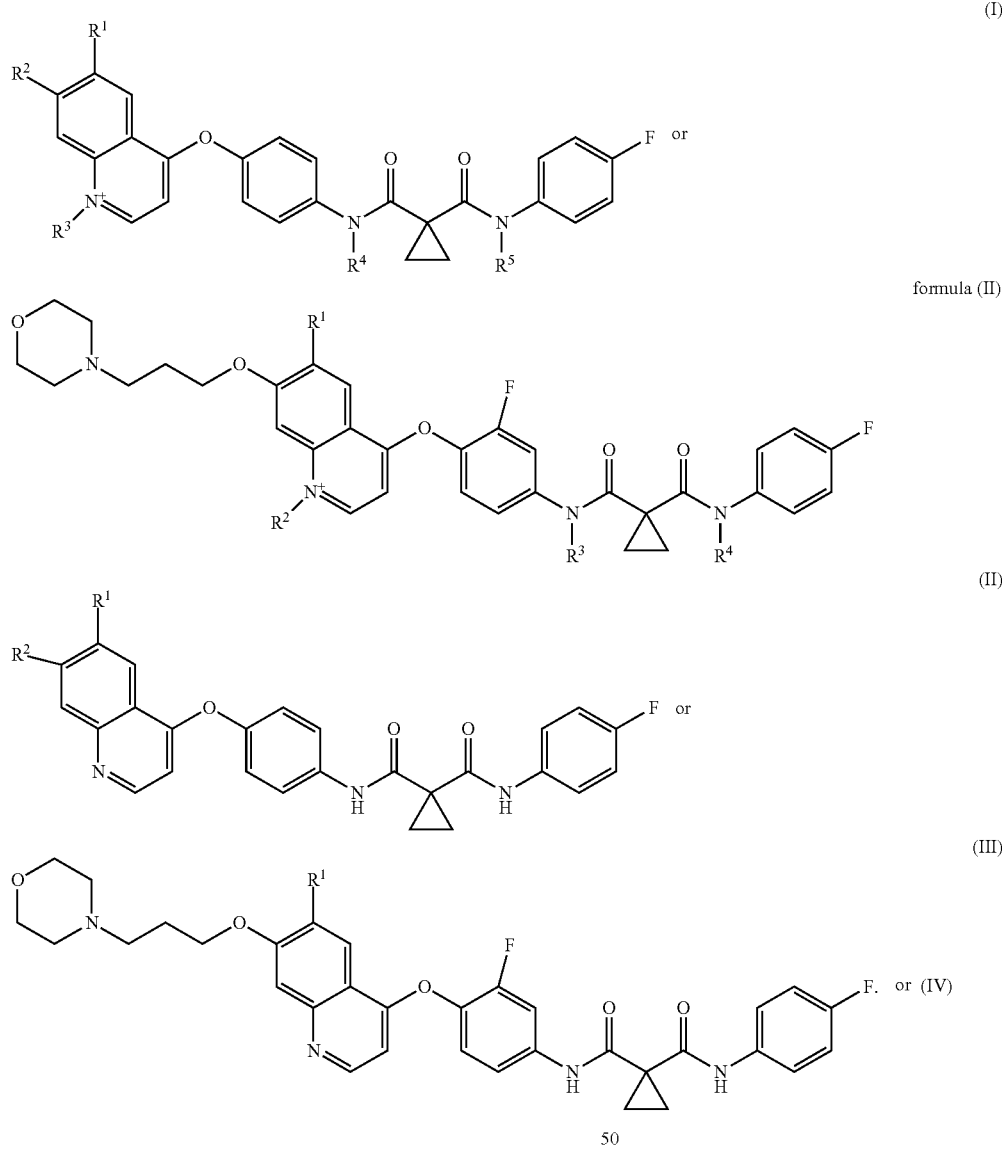

wherein $R^1$, $R^2$, $R^3$, $R^4$ and $R^5$ are each individually selected from absent, hydrogen, oxygen, carbon, potassium, sulfur, phosphorus, nitrogen, —O—CH$_3$, a carbonyl, a sulfhydryl, a phosphatyl, an amide, an amine, a quaternary amine, a phosphate, a phosphonate, a sulfate, a sulfonate, a carboxylate, a urethane and an optionally substituted C2 to C25 alkyl group optionally bound to a peptide or a protein and at least one of $R^1$, $R^2$, $R^3$, $R^4$ and $R^5$ is not absent, hydrogen, oxygen, carbon, potassium, sulfur, phosphorus, nitrogen, —O—CH$_3$, a carbonyl, a sulfhydryl, a phosphatyl, an amide, an amine, a quaternary amine, a phosphate, a phosphonate, a sulfate, a sulfonate, a carboxylate or a urethane.

In a more preferred embodiment the optionally substituted C2 to C25 alkyl group is substituted at a hydrogen or a carbon with one or more substituents selected from the group consisting of an optionally substituted carbonyl, sulfhydryl, phosphate, phosphatyl, phosphonate, amide, amine, quaternary amine, sulfate, sulfonate and carboxylate.

In another more preferred embodiment, the one or more substituents are optionally substituted with a fatty acid or a second alkyl, preferably palmitate.

In another more preferred embodiment, the present invention is directed to a compound of formula (I) wherein $R^1$ is

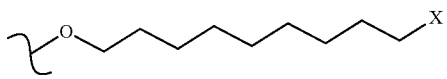

and wherein $R^2$, $R^3$, $R^4$ and $R^5$ are each H and wherein X is a peptide, a protein or absent.

In another more preferred embodiment, the present invention is directed to a compound of formula (I) wherein $R^1$ is

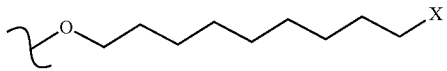

and wherein $R^2$ is O and wherein $R^3$, $R^4$ and $R^5$ are each H and wherein X is a peptide, a protein or absent.

In another more preferred embodiment, the present invention is directed to a compound of formula (I) wherein $R^1$ and $R^2$ are each individually selected from H, O, —O—CH$_3$, —COOH, and an optionally substituted C2 to C25 alkyl group bound to a peptide or a protein and wherein $R^3$, $R^4$ and $R^5$ are each H and wherein at least one of $R^1$ and $R^2$ is not H.

In another embodiment, the present invention is directed to a composition comprising a compound of the present invention and one or more pharmaceutically acceptable excipients.

In another embodiment, the present invention is directed to a method of treating a condition of the eye, preferably selected from diabetic background retinopathy, diabetic macular edema, diabetic proliferative retinopathy, diabetic macular edema with proliferative retinopathy, neovascular glaucoma, retinopathy of prematurity, proliferative fibrovascular disease, diabetic macular edema with proliferative fibrovascular disease, retinopathy of prematurity, dry macular degeneration, any retinopathies with vascular leakage such as Coat's disease or Bescet's disease, dry macular degeneration with drusen and wet macular degeneration, comprising administering via intravitreal injection or topical application of a therapeutically effective amount of a compound of the invention to a subject in need thereof.

In a preferred embodiment administration via intravitreal injection of compounds of the present invention occurs no more than once every 3 months, more preferably once every 6 months and even more preferably once every 9 months.

In another embodiment, the present invention is directed to a method of treating diabetic macular edema comprising administering via intravitreal injection or topical application of a therapeutically effective amount of a compound of the invention to a subject in need thereof, wherein proliferative retinopathy is prevented.

In another embodiment, the present invention is directed to a method of treating diabetic macular edema with proliferative retinopathy comprising administering via intravitreal injection or topical application of a therapeutically effective amount of a compound of the invention to a subject in need thereof, wherein proliferative retinopathy is suppressed.

In another embodiment, the present invention is directed to a method of treating diabetic macular edema comprising administering via intravitreal injection or topical application of a therapeutically effective amount of a compound of the invention to a subject in need thereof, wherein fibrovascular proliferative disease is prevented.

In another embodiment, the present invention is directed to a method of treating diabetic macular edema with fibrovascular proliferative disease comprising administering via intravitreal injection or topical application of a therapeutically effective amount of a compound of the invention to a subject in need thereof, wherein fibrovascular proliferative disease is suppressed.

In another embodiment, the present invention is directed to a method of treating dry macular degeneration or dry macular degeneration with drusen comprising administering via intravitreal injection or topical application of a therapeutically effective amount of a compound of the invention to a subject in need thereof, wherein wet macular degeneration is suppressed or prevented.

In another embodiment, the polar moiety provides binding to vitreous proteins or plasma proteins, preferably albumin, such that treating a condition of the eye requires intravitreal injection or topical application of a therapeutically effective amount of a compound of the invention to a subject in need thereof, wherein the administration occurs no more than once every 3 months, preferably, no more than once every 6 months and more preferably no more than once every 9 months.

DETAILED DESCRIPTION OF THE INVENTION

Intravitreal administration of the MTKI derivatives of the present invention results in a controlled-release of MTKI in the form of a delayed-release or a slow-release (i.e. a sustained-release) resulting in reduced system toxicity and prolonged treatment of eye condition per administration. This controlled-release is achieved by the use of MTKI derivatives containing C2 to C25 alkyl group optionally bound to a peptide or a protein moiety, which bind to endogenous vitreous proteins or plasma proteins, particularly albumin. Once the bound albumin breaks down the moiety then binds to a new endogenous whole albumin protein providing longer half-life than an MTKI bound directly to albumin, which becomes active as soon as the bound albumin breaks down. To treat conditions of the retina, the MTKI derivatives of the present invention bound to albumin are endocytosed by cells of the retinal pigment epithelium layer. This relatively slow degree of hydrolysis and endocytosis results in a very low concentration of MTKI derivative released into the retina over a long period of time.

Further, the long half-life of the MTKI derivatives of the present invention are beneficial for use as an intravenous injection leading to longer plasma duration. The MTKI derivatives of the present invention may also be administered via the oral route. MTKI derivatives of the present invention may lead to higher patient tolerance than MTKI's due to the ability to be absorbed through the intestinal wall without causing major disturbances such as perforation of the colon.

Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used herein, the term "composition" is intended to encompass a product comprising the specified ingredients in the specified amounts, as well as any product which results, directly or indirectly, from a combination of the specified ingredients in the specified amounts.

The terms "treating" and "treatment" refer to reversing, alleviating, inhibiting, preventing, suppressing or slowing the progress of the disease, disorder, or condition to which such terms apply, or one or more symptoms of such disease, disorder, or condition.

As used herein, the term "effective amount" refers to an amount sufficient to affect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful subject benefit. Thus, an "effective amount" will depend upon the context in which it is being administered. An effective amount may be administered in one or more prophylactic or therapeutic administrations.

As used herein, the term "pharmaceutically acceptable" describes a material that is not biologically or otherwise undesirable, i.e., without causing an unacceptable level of undesirable biological effects or interacting in a deleterious manner.

As used herein, the terms "prolonged release" "slow release" and "sustained release" describe release of the active form of a drug over a period of time that starts immediately upon administration of the drug and ends sometime after the administration of the drug.

As used herein, the term "delayed release" describes the release of the active form of a drug that starts after the administration of the drug.

As used herein, the term "controlled release" describes the release of the active form of a drug after the administration of the drug.

As used herein the IC50 measurements for VEGFR2 and c-MET were based on measurements taken in human umbilical vein endothelial cells.

As used herein, the term "substituted" is contemplated to include all permissible substituents of organic compounds. In a broad embodiment, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain embodiments, unless expressly indicated to the contrary, individual substituents can be further optionally substituted (i.e., further substituted or unsubstituted).

The term "alkyl" as used herein is a branched or straight-chain alkyl consisting of a saturated hydrocarbon group of 1 to 25 carbon atoms ($C_1$-$C_{25}$) unless otherwise stated, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or straight-chained. The alkyl group can also be substituted or unsubstituted. For example, the alkyl group can be substituted at hydrogen or carbon atoms with one or more groups including, but not limited to, alkyl, cycloalkyl, alkoxy, amino, ether, halide, hydroxy, nitro, silyl, sulfo-oxo, thiol, a phosphate, a sulfate a carbonyl, a sulfhydryl, a phosphatyl, a phosphonate, an amide, an amine, a quaternary amine, a sulfonate or a carboxylate. Carbon atoms can additionally be substituted with oxygen or nitrogen atoms.

The term "carbonyl" as used herein refers to a compound of the structure

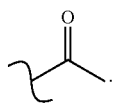

The term "sulfhydryl" as used herein refers to a compound of the structure

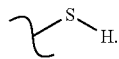

The term "amide" as used herein refers to a compound of the structure

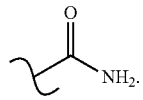

The term "amine" as used herein refers to a compound of the structure

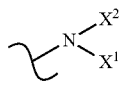

wherein $X^1$ and $X^2$ are each independently an H or an optionally substituted alkyl and wherein at least one of $X^1$ and $X^2$ are not H.

The term "quaternary amine" as used herein refers to a compound of the structure

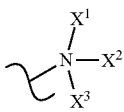

wherein $X^1$, $X^2$ and $X^3$ are each independently an H or an optionally substituted alkyl and wherein at least one $X^1$, $X^2$ and $X^3$ are not H.

The term "phosphate" as used herein refers to a compound of the structure

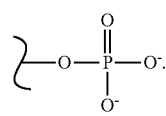

The term "phosphonate" as used herein refers to a compound of the structure

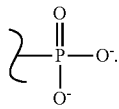

The term "sulfate" as used herein refers to a compound of the structure

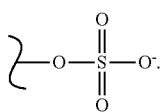

The term "sulfonate" as used herein refers to a compound of the structure

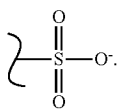

The term "carboxylate" as used herein refers to a compound of the structure

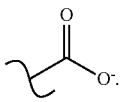

The term "urethane" as used herein refers to a compound of the structure

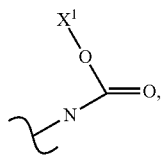

wherein $X^1$, is an H or an optionally substituted alkyl, wherein the optionally substituted alkyl is optionally substituted with

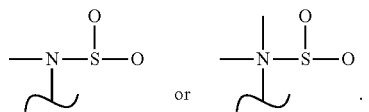

The term "fatty acid" as used herein refers to a compound of the following structure

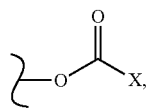

wherein X is a saturated or unsaturated aliphatic chain containing from 2 to 28 carbons.

"$R^1$," "$R^2$," "$R^3$", "$R^4$" and "$R^5$" as used herein, each individually absent or refer to a compound selected from hydrogen, oxygen, carbon, potassium, sulfur, phosphorus, nitrogen, —O—C, a carbonyl, a sulfhydryl, a phosphatyl, an amide, an amine, a quaternary amine, a phosphate, a phosphonate, a sulfate, a sulfonate, a carboxylate, a urethane and an optionally substituted C2 to C25 alkyl group optionally bound to a peptide or a protein wherein the carbonyl, sulfhydryl, phosphatyl, amide, amine, quaternary amine, phosphate, phosphonate, sulfate, sulfonate, carboxylate, urethane are optionally bound to a second alkyl or a fatty acid.

As used herein the term "peptide" refers to a chain of 2 to 49 amino acids bound together via peptide bonds.

As used herein the term "protein" refers to a chain of at least 50 amino acids bound together via peptide bonds and oligomers and polymers thereof.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as 2H, 3H, 13C, 14C, 15N, 18O, 17O, 35S, 18F and 36Cl, respectively. Compounds further comprise prodrugs thereof, and pharmaceutically acceptable salts of said compounds which contain the aforementioned isotopes and/or other isotopes of other atoms are within the scope of this invention. Certain isotopically-labelled compounds of the present invention, for example those into which radioactive isotopes such as 3H and 14C are incorporated, are useful in drug and/or substrate tissue distribution assays. Tritiated, i.e., 3H, and carbon-14, i.e., 14C, isotopes are particularly preferred for their ease of preparation and detectability. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

It is also appreciated that certain compounds described herein can be present as an equilibrium of tautomers. For example, ketones with an α-hydrogen can exist in an equilibrium of the keto form and the enol form.

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Compounds of the Invention

Preferred MTKI's of the present invention are characterized by an IC50 concentration threshold for 50% activity of less than 10 nanomolar ("nM"). Preferred MTKI's of the present invention include those compounds in Table 1.

TABLE 1

| Preferred MTKI's of the present invention | |
|---|---|
| MTKI/IC50 for VEGFR2 | Structure |
| Cabozantinib 0.035 nM | |
| Axitinib 0.200 nM | |
| Cediranib 0.500 nM | |
| Ponatinib 1.500 nM | |

TABLE 1-continued

Preferred MTKI's of the present invention

| MTKI/IC50 for VEGFR2 | Structure |
|---|---|
| Foretinib 2.800 nM | 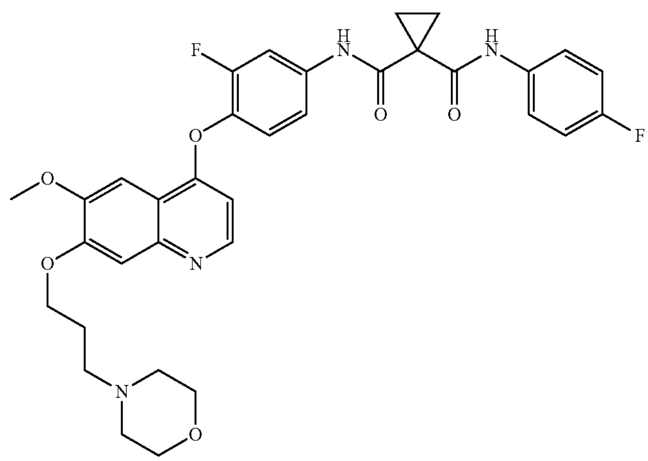 [SMILES: COc1cc2c(Oc3ccc(NC(=O)C4(C(=O)Nc5ccc(F)cc5)CC4)cc3F)ccnc2cc1OCCCN1CCOCC1] |
| MGCD-265 3.000 nM | 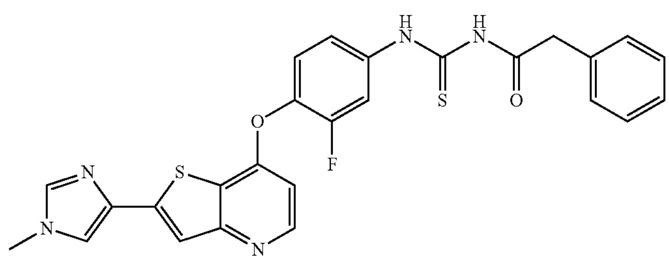 [SMILES: Cn1cnc(-c2cc3nccc(Oc4ccc(NC(=S)NC(=O)Cc5ccccc5)cc4F)c3s2)c1] |
| Motesanib 3.000 nM | 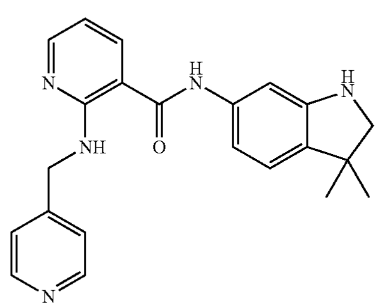 [SMILES: CC1(C)CNc2cc(NC(=O)c3cccnc3NCc3ccncc3)ccc21] |
| Regorafenib 4.200 nM | 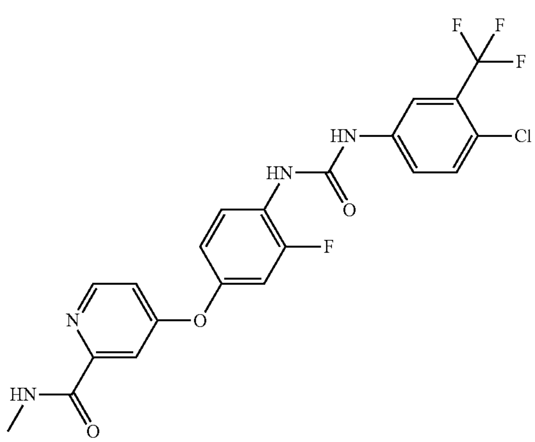 [SMILES: CNC(=O)c1cc(Oc2ccc(NC(=O)Nc3ccc(Cl)c(C(F)(F)F)c3)c(F)c2)ccn1] |

TABLE 1-continued

Preferred MTKI's of the present invention

| MTKI/IC50 for VEGFR2 | Structure |
|---|---|
| Tivozanib 6.500 nM | 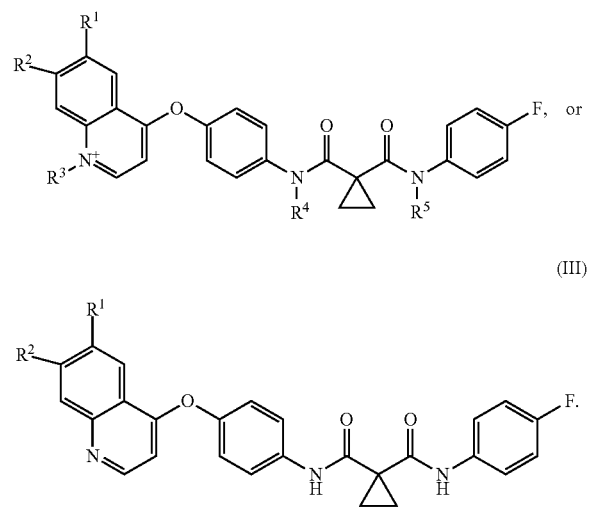 |
| Sunitinib 9.000 nM | 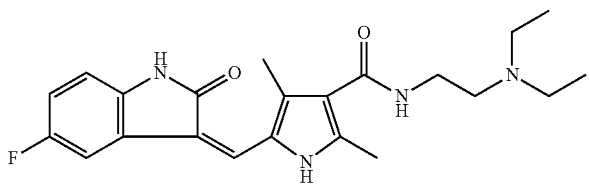 [SMILES: CCN(CC)CCNC(=O)c1c(C)[nH]c(/C=C2\C(=O)Nc3ccc(F)cc32)c1C] |

In another preferred embodiment, preferred moieties include optionally substituted C2 to C25 alkyl groups bound to a peptide or a protein.

In a representative embodiment, cabozantinib derivatives include those of formula (I):

wherein $R^1$, $R^2$, $R^3$, $R^4$ and $R^5$ are each individually selected from absent, hydrogen, oxygen, carbon, potassium, sulfur, phosphorus, nitrogen, —O—CH$_3$, a carbonyl, a sulfhydryl, a phosphatyl, an amide, an amine, a quaternary amine, a phosphate, a phosphonate, a sulfate, a sulfonate, a carboxylate, a urethane, and an optionally substituted C2 to C25 alkyl group optionally bound to a peptide or a protein and at least one of $R^1$, $R^2$, $R^3$ $R^4$ and $R^5$ is not absent, hydrogen, oxygen, carbon, potassium, sulfur, phosphorus, nitrogen, —O—C, a carbonyl, a sulfhydryl, a phosphatyl, an amide, an amine, a quaternary amine, a phosphate, a phosphonate, a sulfate, a sulfonate, a carboxylate, or a urethane.

In a more preferred embodiment the optionally substituted C2 to C25 alkyl group is substituted with one or more substituents selected from the group consisting of an optionally substituted carbonyl, sulfhydryl, phosphate, phosphatyl, phosphonate, amide, amine, quaternary amine, sulfate, sulfonate and carboxylate.

In another more preferred embodiment, the one or more substituents are optionally substituted with a fatty acid or a second alkyl, preferably palmitate.

Representative compounds of formula (I) or (III) include:

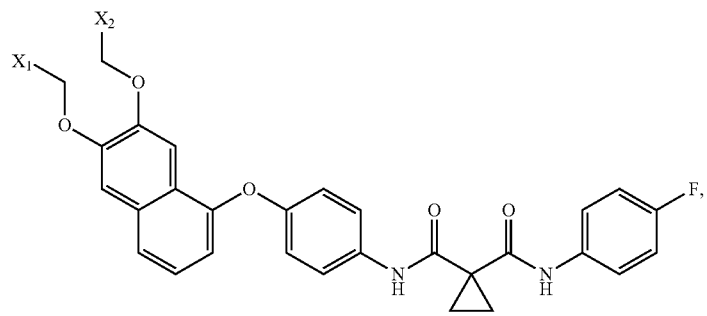

-continued
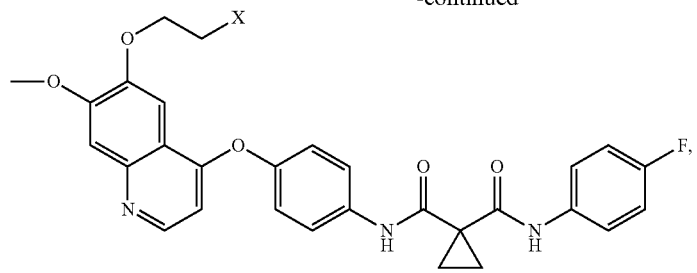
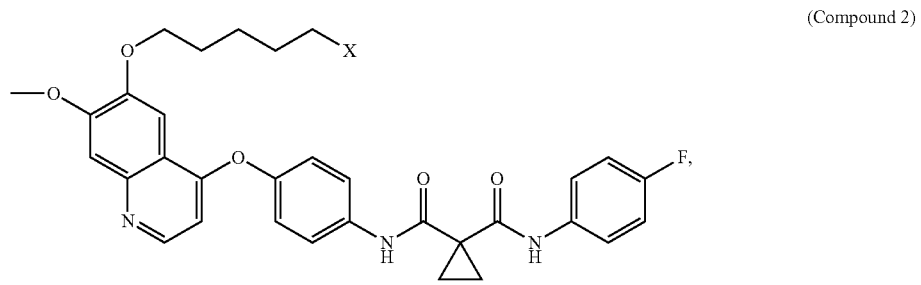
(Compound 2)
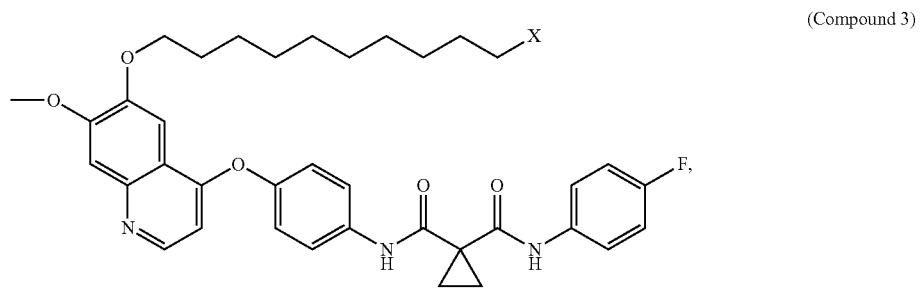
(Compound 3)
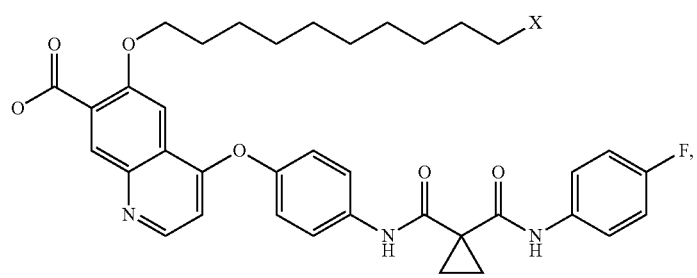
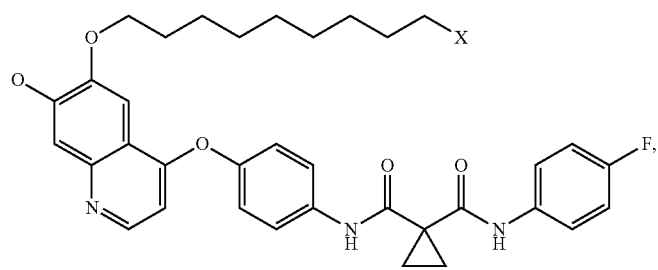

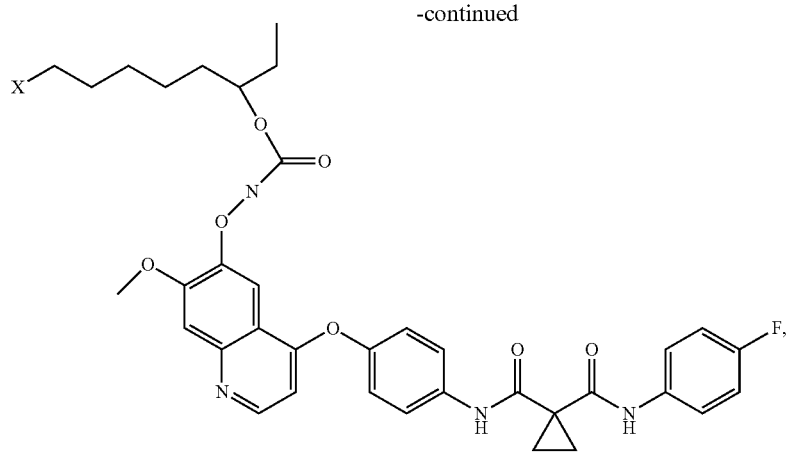
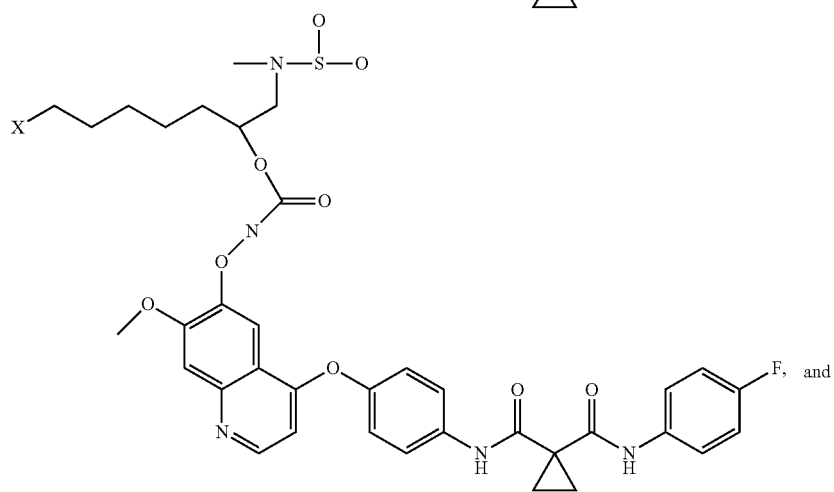
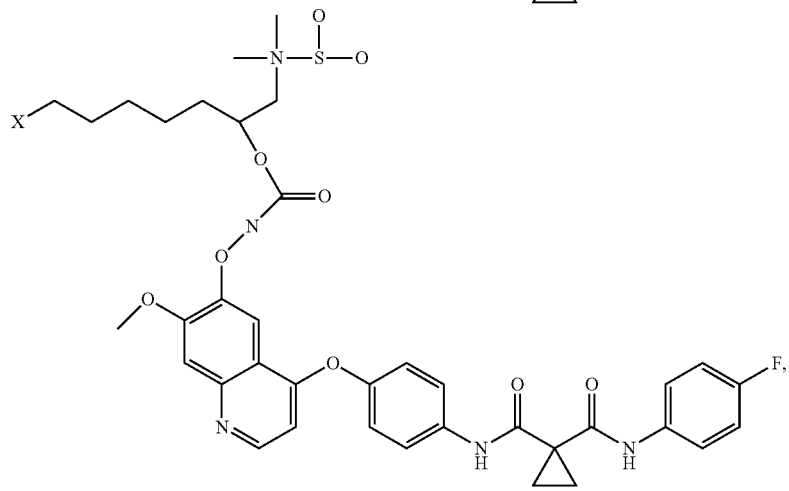
wherein X, $X_1$ and $X_2$ are each, individually a peptide, a protein or absent.
In another representative embodiment, the present invention is directed to a compound of a formula (V):
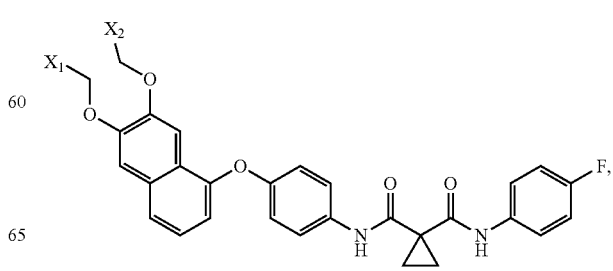

wherein $X_1$ and $X_2$ are each, individually a peptide, a protein or absent.

Further, representative compounds of formula (I) include those in Table 2 below.

TABLE 2

Representative Cabozantinib Derivatives

| Derivative | Name and Estimated Log P Value |
|---|---|
| (structure) | Cabozantinib N-acyl methyl palmitate Estimated log P of 6.77 |
| (structure) | Cabozantinib N-acyl methyl oleate Estimated log P of 6.28 |
| (structure) | Cabozantinib sulfate |

TABLE 2-continued
Representative Cabozantinib Derivatives
| Derivative | Name and Estimated Log P Value |
|---|---|
| 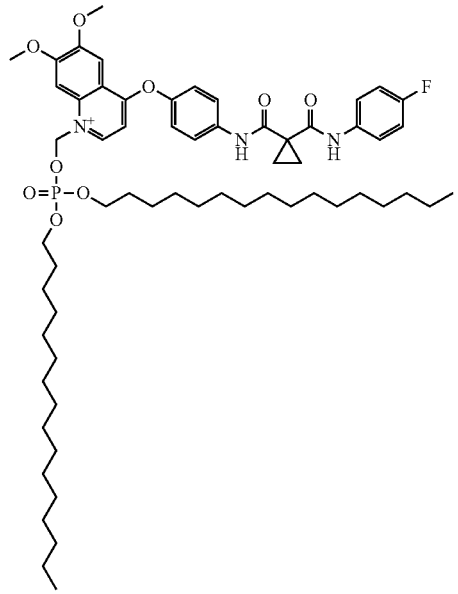 [SMILES: CCCCCCCCCCCCCCCCOP(=O)(OCCCCCCCCCCCCCCCC)OC[n+]1ccc(Oc2ccc(NC(=O)C3(C(=O)Nc4ccc(F)cc4)CC3)cc2)c2cc(OC)c(OC)cc21] | Cabozantinib phosphodipalmitate |
| 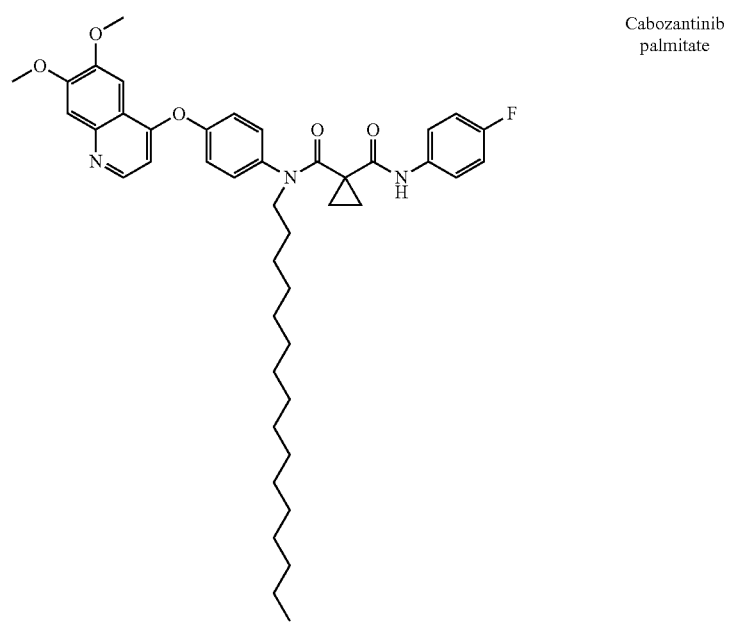 | Cabozantinib palmitate |

TABLE 2-continued

Representative Cabozantinib Derivatives

| Derivative | Name and Estimated Log P Value |
|---|---|
| [chemical structure] | Cabozantinib palmitate |
| [chemical structure] (Compound 4). | |

Compositions of the Invention

The selection of MTKI derivatives for slow and/or delayed conversion can be enhanced by selection of compositions to aid in slow and/or delayed release, such as nanosuspensions or nanoencapsulation. For nanosuspensions, methods well known to experts in the art such as milling or formulation via supercritical solutions may be used. Preferred nanosuspensions have particle size of less than 400 nM, preferably less than 150 nM and more preferably between 50 and 100 nM. For saline nanosuspensions, less than 1 mg/ml of a compound of the present invention is formulated with a particle size from about 50 to about 300 nM. Preferred nanoencapsulation is achieved through the use of a caprylactone polymer, though poly(D,L-lactide-co-glycolide) ("PLGA") and PLGA-alpha tocopherol or other encapsulation polymers may be used. Preferred emulsions allow for substantially greater than 1% oil to be combined with the water phase. For example, a 50:50 oil in water ratio is sufficient for intravitreal drug delivery. Double emulsions of the present invention include, but are not limited to, oil-in-water-in-water and water-in-oil-in-water double emulsions.

Compositions of the present invention also include the use of nanoparticles, microparticles, nanocapsules, microcapsules, nanospheres and microspheres. Processes for preparing nanoparticles and double emulsions are detailed in Song K. C., et al., The effect of type of organic phase solvents on particle size of poly(D,L-lactide-co-glycolide) nanoparticles, *Colloids Surf A Phsyiochem Eng Aspects,* 2006, 276, 162-167, and in U.S. Patent Application Publication No. 2013/0209566, each of which are incorporated by reference in its entirety. Processes for preparing microspheres are detailed in Alhenn D. et al., Microsphere preparation using the nontoxic solvent glycofurol, *Pharm Res,* 2011, March, 28 (3), 563-571, which is incorporated by reference in its entirety. Processes for preparing an oil-in-water emulsion are detailed in Daull et al., A preliminary evaluation of dexamethasone palmitate emulsion: a novel intravitreal sustained delivery of corticosteroid for treatment of macular edema, *J Ocul Pharmacol Ther,* 2013 March, 29(2), 258-269, which is incorporated by reference in its entirety.

Compositions of the present invention may be formulated as emulsions or microemulsions. Processes for preparing emulsions and microemulsions are well known in the art and include commercial lipoemulsions such as Intralipid® (Intralipid is a registered trademark of Fresenius Kabi AB), Abbolipid and SolEmuls® as described in Muller R H, et al., SolEmuls-novel technology for the formulation of i.v. emulsions with poorly soluble drugs, *Int J Pharm,* 2004 Jan. 28, 269(2), 293-302.

Compositions of the present invention include excipients not limited to antioxidants, surfactants, viscosity enhancers, tonicity adjustors, osmolality modifiers, solubility enhancers, preservatives and buffers.

Antioxidants suitable for the present invention include, but are not limited to, alpha tocopherol, sodium metabisulfite, sodium thiosulfate, acetylcysteine, butylated hydroxyanisole and butylated hydroxytoluene.

Surfactants suitable for the present invention include, but are not limited to, nonionic, cationic and/or anionic surfactants. Specific surfactants include cyclodextrins, polyoxyl alkyls, poloxamers or combinations thereof. Preferred nonionic surfactants include tyloxapol, alpha cyclodextrin, beta cyclodextrin, gamma cyclodextrin, a poloxamer, a polysorbate and a polyoxyl stearate Further, substitution of other surfactants compatible with ophthalmic use allows for similar composition advantages, which may included but is not limited to one or more of a nonionizing surfactant such as poloxamer, Poloxamer 188, Poloxamer 407, Polysorbate 20, Polysorbate 80, ionically charged (e.g. anionic) beta-cyclodextrins with or without a butyrated salt (Captisol®; (sulfobutylether β-cyclodextrin, Captisol is a registered trademark of Cydex Pharmaceuticals), 2-hydroxypropyl beta cyclodextrin ("HPβCD"), Polyoxyl 35 stearate, Polyoxyl 40 castor oil and Polyoxyl 40 hydrogenated castor oil, poloxamer 103, poloxamer 123, and poloxamer 124, poloxamer 407, poloxamer 188, and poloxamer 338, any poloxamer analogue or derivative, polysorbate, polysorbate 20, polysorbate 40, polysorbate 60, polysorbate 80, any polysorbate analogue or derivative, cyclodextrin, hydroxypropyl-β-cyclodextrin, hydroxypropyl-γ-cyclodextrin, randomly methylated β-cyclodextrin, β-cyclodextrin sulfobutyl ether, γ-cyclodextrin sulfobutyl ether or glucosyl-β-cyclodextrin, any cyclodextrin analogue or derivative, polyoxyethylene, polyoxypropylene glycol, an polysorbate analogue or derivative, polyoxyethylene hydrogenated castor oil 60, polyoxyethylene (200), polyoxypropylene glycol (70), polyoxyethylene hydrogenated castor oil, polyoxyethylene hydrogenated castor oil 60, polyoxyl, polyoxyl stearate, nonoxynol, octyphenol ethoxylates, nonyl phenol ethoxylates, capryols, lauroglycol, PEG such as PEG400, Brij® 35(polyoxyethyleneglycol dodecyl ether; Brij is a registered trademark of Uniqema Americas LLC), glyceryl laurate, lauryl glucoside, decyl glucoside, or cetyl alcohol; or zwitterion surfactants such as palmitoyl carnitine, cocamide DEA, cocamide DEA derivatives cocamidopropyl betaine, or trimethyl glycine betaine, N-2(2-acetamido)-2-aminoethane sulfonic acid (ACES), N-2-acetamido iminodiacetic acid (ADA), N,N-bis(2-hydroxyethyl)-2-aminoethane sulfonic acid (BES), 2-[Bis-(2-hydroxyethyl)-amino]-2-hydroxymethyl-propane-1,3-diol (Bis-Tris), 3-cyclohexylamino-1-propane sulfonic acid (CAPS), 2-cyclohexylamino-1-ethane sulfonic acid (CHES), N,N-bis (2-hydroxyethyl)-3-amino-2-hydroxypropane sulfonic acid (DIPSO), 4-(2-hydroxyethyl)-1-piperazine propane sulfonic acid (EPPS), N-2-hydroxyethylpiperazine-N'-2-ethane sulfonic acid (HEPES), 2-(N-morpholino)-ethane sulfonic acid (MES), 4-(N-morpholino)-butane sulfonic acid (MOBS), 2-(N-morpholino)-propane sulfonic acid (MOPS), 3-morpholino-2-hydroxypropanesulfonic acid (MOPSO), 1,4-piperazine-bis-(ethane sulfonic acid) (PIPES), piperazine-N,N-bis(2-hydroxypropane sulfonic acid) (POPSO), N-tris(hydroxymethyl)methyl-2-aminopropane sulfonic acid (TAPS), N-[tris(hydroxymethyl)methyl]-3-amino-2-hydroxypropane sulfonic acid (TAPSO), N-tris(hydroxymethyl) methyl-2-aminoethane sulfonic acid (TES), 2-Amino-2-hydroxymethyl-propane-1,3-diol (Tris), tyloxapol, Span® 20-80 (sorbitan monolaurate, sorbitan monopalmitate, sorbitan monostearate, and sorbitan monooleate; Span is a registered trademark of Uniqema Americas Inc.), Tween® 20 (Tween is a registered trademark of Uniqema Americas LLC), Tween® 80, Labrasol® (caprylocaproyl macrogol-8 glycerides; Labrasol is a registered trademark of Gattefosse SAS). Surfactants of the present invention can be at a concentration from about 0.01% to about 99% w/v, preferably from about 1% to about 30% w/v.

Solubility enhancers (i.e. solvents) suitable for the present invention include, but are not limited to, glycofurol (a.k.a. tetraglycol and tetraethylene glycol), dimethyl sulfoxide ("DMSO"), vitamin E TPGS (d-alpha tocopherol polyethylene glycol 1000 succinate), dimethyl sorbide ("DMI"), ethyl acetate, acetonitrile, ethyl alcohol, alcohols, polyols, amides, esters, polyethylene glycol, propylene glycol, propylene glycol ethers, polysorbates, poloxamers, cyclodextrins, Span® 20-80, dimethyl isosorbide, isopropyl myristate oil and complexing agents such as cyclodextrins and nicotinamide or a combination thereof. Solubility enhancers of the present invention can be at a concentration from about 0.01% to about 99% w/v, preferably from about 1% to about 30% w/v.

Viscosity enhancers suitable for the present invention include, but are not limited to, carboxymethyl cellulose ("CMC"), methylcellulose, methyl cellulose 4000, hydroxymethyl cellulose, hydroxypropyl cellulose, hydroxypropylmethyl cellulose, hydroxyl propyl methyl cellulose 2906, carboxypropylmethyl cellulose, hydroxyethyl cellulose, or hydroxyethyl cellulose, hyaluronic acid, dextran, polyethylene glycol, polyvinyl alcohol, polyvinyl pyrrolidone, gellan, carrageenan, alignic acid, carboxyvinyl polymer or combinations thereof. Viscosity enhancers of the present invention can be at a concentration from about 0.01% to about 99% w/v, preferably from about 0.1% to about 10% w/v.

A tonicity adjustor can be, without limitation, a salt such as sodium chloride ("NaCl"), potassium chloride, mannitol or glycerin, or another pharmaceutically or ophthalmically acceptable tonicity adjustor. Tonicity adjustors of the present invention can be at a concentration from about 0.01% to about 99% w/v, preferably from about 0.1% to about 10% w/v.

Osmolality modifiers suitable for the present invention include, but are not limited to, mannitol, sorbitol, glycerol and a combination thereof. Osmolality modifiers of the present invention can be at a concentration from about 0.01% to about 99% w/v, preferably from about 0.1% to about 10% w/v.

Preservatives that can be used with the present invention include, but are not limited to, benzalkonium chloride (BAK), chlorobutanol, thimerosal, phenylmercuric acetate, disodium ethylenediaminetetraacetic acid, phenylmercuric nitrate, perborate or benzyl alcohol. In a preferred embodiment the preservative is BAK at a concentration of about 0.001% to about 1.0% w/v, more preferably at a concentration of about 0.02% w/v.

Various buffers and means for adjusting pH can be used to prepare ophthalmological compositions of the invention. Such buffers include, but are not limited to, acetate buffers, citrate buffers, citric acid buffers, phosphate buffers and borate buffers. It is understood that acids or bases can be used to adjust the pH of the composition as needed, preferably of 1 to 10 mM concentration, and more preferably about 5 mM. In a preferred embodiment the pH is from about 3.0 to about 8.0, in a more preferred embodiment the pH is from about 7.0 to about 7.5.

In another embodiment, compositions of the present invention comprise polylactide polymers. Polylactide polymers suitable for the present invention include, but are not limited to, polylactic acid, poly-L-lactide, poly-D-lactide, poly(D,L-lactide) poly(L-lactide-co-D,L-lactide) and poly(D,L-lactide-co-glycolide).

Diseases to Be Treated With Compounds, Compositions and Methods of the Invention Diseases that may be treated by compositions and methods of the present invention include ophthalmic conditions, but are not limited to:

A) Maculopathies/Retinal degenerations including non-exudative (dry) age-related macular degeneration ("AMD"), prophylactic treatment of severe dry AMD to prevent onset of wet AMD, exudative (wet) AMD, choroidal neovascularization, diabetic retinopathy, particularly prophylactically in the treatment of background diabetic retinopathy to prevent diabetic macular edema and or proliferative retinopathy, the treatment prophylactically of proliferative retinopathy to prevent vitreous hemorrhage, and particularly preferentially in the presence of proliferative retinopathy where conventional treatments (antibody anti-VEGF) may induce increased fibrovascular change with contraction along the retina and possible retinal detachment, acute macular neuroretinopathy, central serous chorioretinopathy, cystoids macular edema and macular edema;

B) Uveitis/Retinitis/Choroiditis including acute multifocal placoid pigment epitheliopathy, Behcet's disease, Birdshot retinochoroidopathy, infectious (syphilis, lime, tuberculosis, toxoplasmosis), intermediate uveitis (pars planitis), multifocal choroiditis, multiple evanescent white dot syndrome, ocular sarcoidosis, posterior scleritis, serpiginous choroiditis, subretinal fibrosis, uveitis syndrome, and Vogt-Koyanagi-Harada syndrome;

C) Vascular diseases/Exudative diseases including Coat's disease, parafoveal telangiectasis, papillophlebitis, frosted branch angitis, sickle cell retinopathy, other hemoglobinopathies, angioid streaks and familial exudative vitreoretinopathy;

D) Traumatic/surgical diseases including sympathetic ophthalmia, uveitic retinal disease, retinal detachment, trauma from laser photocoagulation or photodynamic therapy, hypoperfusion during surgery, radiation retinotherapy and bone marrow transplant retinopathy;

E) Proliferative disorders including proliferative vitreal retinotherapy, epiretinal membranes, proliferative diabetic retinopathy and retinopathy of prematurity (retrolental fibroplastic);

F) Infectious disorders including ocular histoplasmosis, ocular toxocariasis, presumed ocular histoplasmosis syndrome, endophthalmitis, toxoplasmosis, retinal diseases associated with HIV infection, choroidal disease associated with HIV infection, uveitic disease associated with HIV infection, viral retinitis, acute retinal necrosis, progressive outer retinal necrosis, fungal retinal diseases, ocular syphilis, ocular tuberculosis, diffuse unilateral subacute neuroretinitis and myiasis;

G) Genetic disorders including systemic disorders with associated retinal dystrophies, congenital stationary night blindness, cone dystrophies, fundus flavimaculatus, Best's disease, Pattern dystrophy of the retinal pigmented epithelium, X-linked retinoschisis, Sorsby's fundus dystrophy, benign concentric maculopathy, Bietti's crystalline dystrophy, psuedoxanthoma elasticum and Osler Weber syndrome;

H) Retinal tears/holes including retinal detachment, macular hole and giant retinal tear;

I) Tumors including retinal disease associated with tumors, solid tumors, tumor metastasis, benign tumors (e.g. hemangiomas, neurofibromas, trachomas, pyogenic granulomas), congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma and intraocular lymphoid tumors;

J) Neovascular ischemia including neovascular glaucoma, anterior segment ischemia syndromes, corneal neovascularization including post corneal surgery such as post penetrating keratoplasty, herpetic keratitis and other ischemic or corneal inflammatory conditions; and K) Other diseases that may be treated by compositions and methods of the present invention include cancers not limited to chronic myeloid leukemia ("CML"), acute lymphocytic leukemia, non-small cell lung cancer, pancreatic cancer, gastrointestinal stromal tumors, hypereosinophilic syndrome, systemic mastocytosis, breast cancer with HER2/ neu overexpression, chronic phase or accelerated Ph-positive CML, renal cell cancer, and hepatocellular carcinoma.

In one embodiment, the present invention is directed to oral administration of a compound of the present invention to a subject in need thereof.

In another embodiment, the present invention is directed to intravenous injection of a compound of the present invention to a subject in need thereof.

Diabetic retinopathy in particular may be therapeutically improved or worsened by conventional anti-VEGF therapies (antibody ant-VEGF including Lucentis®, Eylea®), where background retinopathy leading to macular edema may be improved. With the onset of proliferative retinopathy however conventional anti-VEGF therapy causes increased fibrosis. Van Geest R. J. et al., A shift in the balance of vascular endothelial growth factor and connective tissue growth factor by bevacizumab causes the angiofibrotic switch in proliferative diabetic retinopathy *Br J Ophthalmol*, 2012 April, 96(4), 587-90. It is a surprising and previously unrecognized virtual discovery that intravitreal injection of preferred embodiments cabozantinib N-acyl methyl palmitate and foretinib N-acyl methyl palmitate suppress intraocular proliferative retinopathy, and most particularly diabetic proliferative retinopathy. The suppression of intraocular proliferative retinopathy in turn suppresses fibrotic induction and the most severe manifestations of proliferative eye disease. This suppression also is virtually discovered to occur when the methyl of the preferred embodiments is replaced by any alkyl group. It is of not that N-acyl methyl palmitate and foretinib N-acyl methyl palmitate, without or without substitution of the methyl group are virtually discovered to suppress VEGFR and c-MET. Proliferative retinopathy progression to fibrovascular proliferation has extremely high morbidity with changes including but not limited to fibrovascular traction, vitreofibrosis, macular pucker and related distortion, epiretinal membranes with induced retinal shear, retinal detachment, increased morbidity with intravitreal injection and poor prognosis after vitrectomy with or without dissection of epiretinal membranes and separation and treatment of fibrovascular membranes. As diabetic macular edema is amenable to anti-VEGF therapy, its use in patients with preproliferative severe peripheral ischemic disease, and or patients with early proliferative disease may enhance the onset of fibrovascular proliferative morbidity, whereas the present invention using MTKIs combining VEGF suppression with c-MET suppression may both reduce diabetic macular edema and suppress diabetic fibrovascular proliferation.

The following Examples are provided solely for illustrative purposes and are not meant to limit the invention in any way.

EXAMPLES

Example 1

Synthesis of Cabozantinib N-Acyl Methyl Palmitate

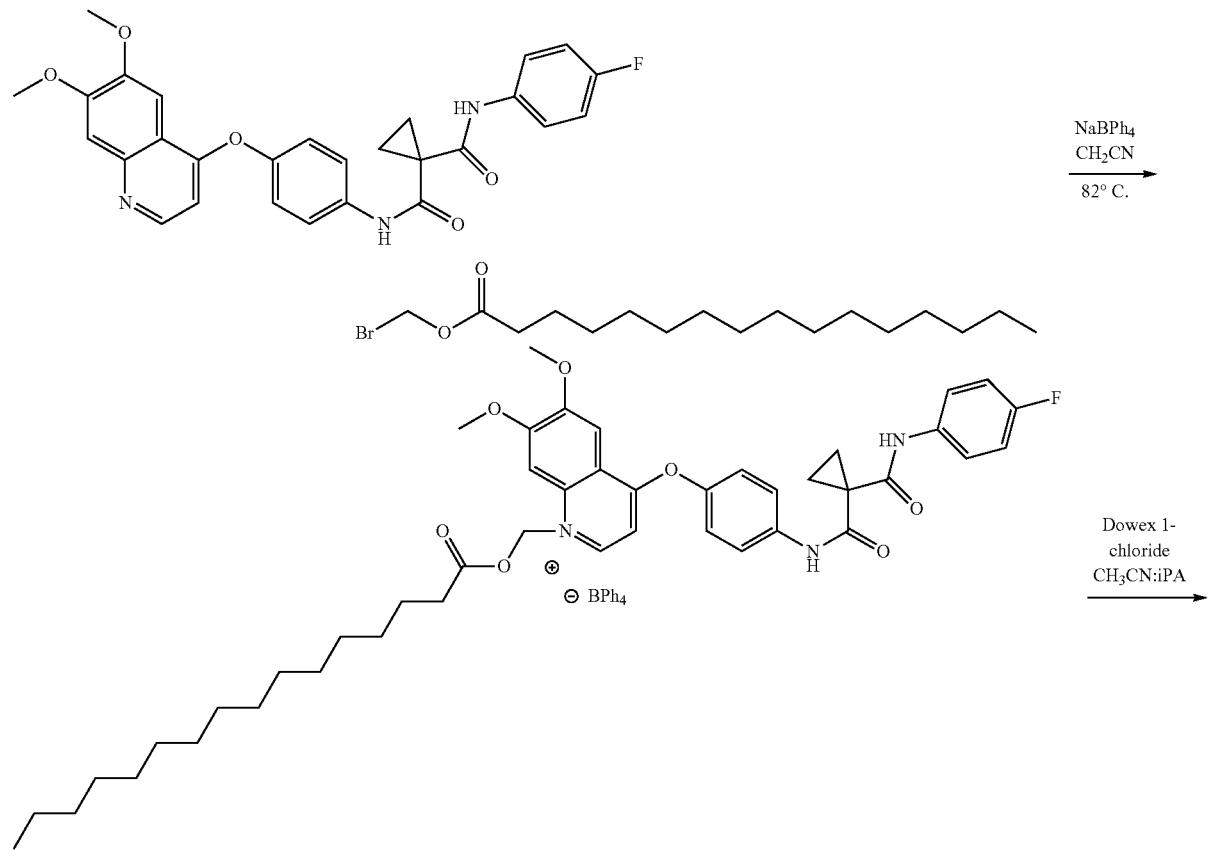

-continued

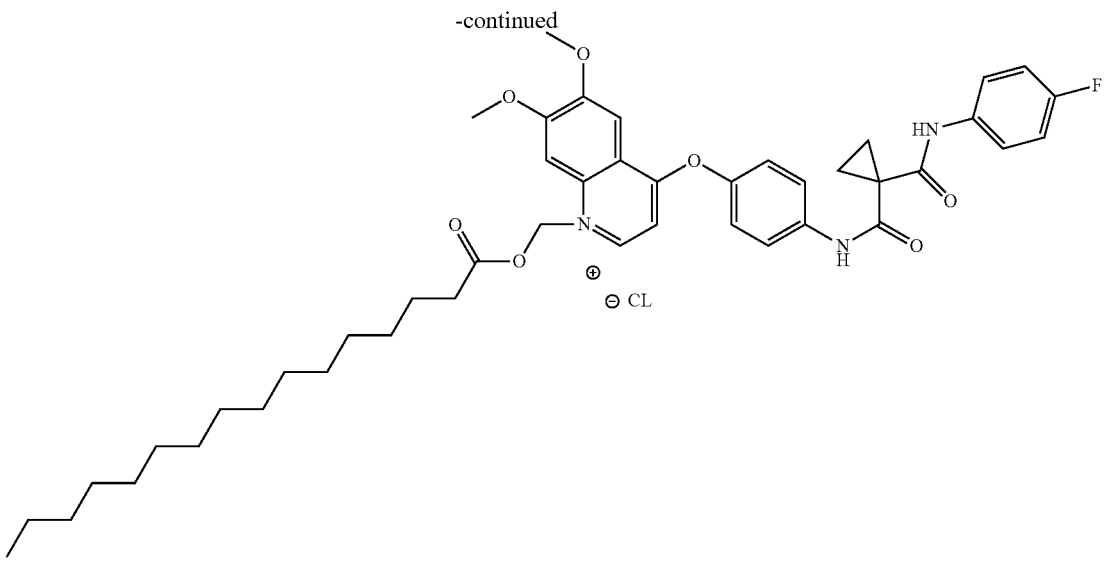

Method

Cabozantinib was incubated with bromomethyl palmitate in the presence of tetraphenylborate ("NaBPh$_4$"), acetonitrile ("CH$_3$CN") at 82° C. for X hours resulting in cabozantinib N-acyl methyl palmitate tetraphenylborate. The cabozantinib N-acyl methyl palmitate tetraphenylborate is then incubated with Dowex®-1-chloride (Dowex is a registered trademark of Dow Chemical Company) and acetonitrile:isopropyl alcohol (iPA) to yield cabozantinib N-acyl methyl palmitate chloride.

Example 2 (Virtual)

Formulation

Cabozantinib N-acyl methyl palmitate (CNAMP) was formulated for intravitreal injection using isopropyl myristate or oleic acid combined with about 10% w/v cyclodextrin and from about 10% to about 30% w/v D-alpha tocopherol PEG 1000 succinate ("TGPS") which were then solubilized via well-known oil solubilization techniques to create a first solution. The first solution was then added to a saturated fatty acid (e.g. octanoic acid) combined with lecithin or lecithin derivatives (e.g. phosphatidyl choline), a glycerol fatty acid ester (e.g. propylene glycol fatty acid esters such as polyoxyethyleneglycerol triricinoleate), a sorbitan fatty acid ester (e.g. Span® 20, Span® 80) or a olyoxylethylene sorbitan fatty acid ester (e.g. Tween® 20, Tween® 80), and optionally a co-surfactant (e.g. propylene glycol, glycerol, PEG 400, 1,2-propanediol), which were then solubilized as a microemulsion using commercial lipoemulsion techniques (e.g. Intralipid®, Abbolipid).

Method 50 uL of an oil or emulsion containing about 10 mg/mL to 20 mg/mL of cabozantinib N-acyl methyl palmitate was administered via midvitreal injection into one eye of a mammal (preferably a pigmented rabbit or a primate). 50 uL of either Lucentis® or Eylea® was administered into the remaining eye of the mammal.

2 weeks after administration a subretinal choroidal neovascularization (CNV) was caused in the eyes of the mammal using techniques explained in Qui G et al., A new model of experimental subretinal neovascularization in the rabbit, *Exp Eye Res,* 2006 July, 83(1), 141-152. 6 weeks after subretinal CNV eyes of the mammal were sacrificed for examination.

Results

Greater suppression of fibrovascular proliferation will be found in the eye with intravitreal injection of cabozantinib N-acyl methyl palmitate. In addition, a long-lasting suppression of macular edema will be found.

Example 3. In-Vitro Kinase Inhibition Assay

Method

Compounds 2-4 and cabozantinib were each tested for binding of c-Met, VEGFR2, TIE2 and the control compound, staurosporine. Specifically, each compound was tested at a 3-fold serial dilution starting at 10 microMolar ("µM") in a 10-dose IC50 mode into an enzyme/substrate mixture using acoustic technology, and pre-incubated for 20 minutes to ensure compounds were equilibrated and bound to the enzyme. Staurosporine was used as a control and was tested at a 4-fold serial dilution starting at 20 µM. Next, 5 concentrations of ATP were added to initiate the reaction. The activity was monitored every 5-15 min for a time course study.

TABLE 3

IC50 Data for Compound 2 on Various Kinases

| Kinase | [ATP] (µM): | Compound IC50* (M): | | |
|---|---|---|---|---|
| | | Staurosporine | Cabozantinib | Compound 2 |
| c-Met | 10 | 2.16E−07 | <5.08E−10 | 3.76E−06 |
| VEGFR2 | 20 | 1.86E−08 | <5.08E−10 | |
| TIE2 | 30 | 1.20E−07 | 4.90E−07 | |

*Empty cells indicate no inhibition or compound activity that could not be fit to an IC50 curve for any of the 3 kinases.

Results

As can be seen in Table 3, Compound 2 provided significant inhibition of c-Met. Compounds 3 and 4 either demonstrated no inhibition or their activity that could not be fit to an IC50 curve for any of the 3 kinases.

What is claimed is:

1. A method of treating a condition of the eye comprising administering via intravitreal injection or topical application of a therapeutically effective amount of a compound of formula (V):

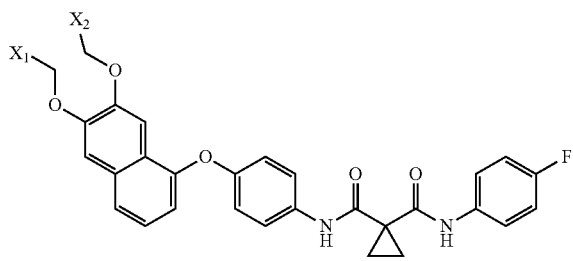

to a subject in need thereof, wherein $X_1$ and $X_2$ are each, individually a peptide, a protein or absent.

2. The method of claim 1, wherein the condition is selected from diabetic background retinopathy, diabetic macular edema, diabetic proliferative retinopathy, diabetic macular edema with proliferative retinopathy, neovascular glaucoma, retinopathy of prematurity, proliferative fibrovascular disease, diabetic macular edema with proliferative fibrovascular disease, retinopathy of prematurity, dry macular degeneration, any retinopathies with vascular leakage such as Coat's disease or Bescet's disease, dry macular degeneration with drusen and wet macular degeneration.

3. The method of claim 1, wherein the condition is diabetic macular edema and wherein proliferative retinopathy is prevented.

4. The method of claim 1, wherein the condition is diabetic macular edema with proliferative retinopathy and proliferative retinopathy is suppressed.

5. The method of claim 1, wherein the condition is diabetic macular edema and wherein fibrovascular proliferative disease is prevented.

6. The method of claim 1, wherein the condition is diabetic macular edema with fibrovascular proliferative disease and wherein fibrovascular proliferative disease is suppressed.

7. The method of claim 1, wherein the condition is dry macular degeneration or dry macular degeneration with drusen and wherein wet macular degeneration is suppressed or prevented.

8. A method of treating a condition of the eye comprising administering via intravitreal injection or topical application of a therapeutically effective amount of a compound of formula (V):

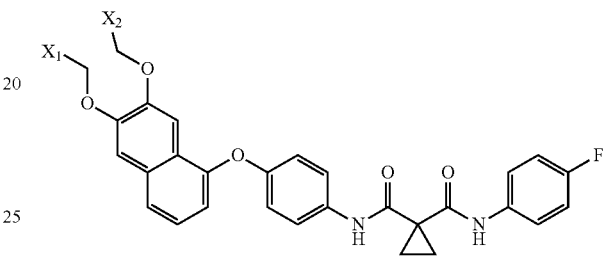

to a subject in need thereof, wherein $X_1$ and $X_2$ are each, individually a peptide, a protein or absent and wherein the administration occurs no more than once every 3 months.

9. The method of claim 8, wherein the administration occurs no more than once every 6 months.

10. The method of claim 8, wherein the administration occurs no more than once every 9 months.

* * * * *